United States Patent
Von Oepen et al.

(10) Patent No.: US 8,246,670 B2
(45) Date of Patent: Aug. 21, 2012

(54) CATHETER SYSTEM AND METHOD FOR DELIVERING MEDICAL DEVICES

(75) Inventors: Randolf Von Oepen, Los Altos, CA (US); Thomas Michael Rieth, Hirrlingen (DE); Lorcan James Coffey, Tubingen (DE); Richard Roy Newhauser, Redwood City, CA (US); Travis Richard Yribarren, Coarsegold, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1239 days.

(21) Appl. No.: 11/844,313

(22) Filed: Aug. 23, 2007

(65) Prior Publication Data

US 2008/0051869 A1    Feb. 28, 2008

Related U.S. Application Data

(60) Provisional application No. 60/823,351, filed on Aug. 23, 2006.

(51) Int. Cl.
*A61F 2/06* (2006.01)

(52) U.S. Cl. .................................................. 623/1.11

(58) Field of Classification Search ............... 623/1.11, 623/1.12; 604/101.02, 101.04, 101.05, 103, 604/103.04; 606/192, 194
See application file for complete search history.

(56) References Cited

U.S. PATENT DOCUMENTS

| 5,607,444 | A |   | 3/1997  | Lam |
| 5,669,924 | A | * | 9/1997  | Shaknovich ................. 623/1.11 |
| 5,749,825 | A |   | 5/1998  | Fischell et al. |
| 5,755,735 | A |   | 5/1998  | Richter et al. |
| 5,868,777 | A |   | 2/1999  | Lam |
| 5,961,548 | A |   | 10/1999 | Shmulewitz |
| 6,017,363 | A |   | 1/2000  | Hojeibane |
| 6,033,434 | A |   | 3/2000  | Borghi |
| 6,099,497 | A |   | 8/2000  | Adams et al. |
| 6,117,117 | A | * | 9/2000  | Mauch .......................... 604/284 |
| 6,117,156 | A |   | 9/2000  | Richter et al. |

(Continued)

FOREIGN PATENT DOCUMENTS

DE    10124107    2/2009

(Continued)

OTHER PUBLICATIONS

International Search Rep. For PCT/US2007/076694, filed Aug. 23, 2007 mailed Jan. 25, 2008 14 pgs.

*Primary Examiner* — Gary Jackson
*Assistant Examiner* — Amy Shipley
(74) *Attorney, Agent, or Firm* — Fulwider Patton LLP

(57) ABSTRACT

A system for delivering a medical device, such as an angioplasty balloon, includes two catheter shafts. The distal portion of a first shaft includes a first balloon and is narrower than the proximal portion. A second catheter shaft includes a second balloon and is connected to a medial portion of the first shaft. The second shaft includes a guidewire passageway which is in communication with the passageway of a third shaft that is removably connected to the first shaft. The distal tips of the first and second balloons are connected together to allow the system to be advanced to an anatomical site using a single guidewire. A second guidewire may be used to separate the distal ends of the balloons and to position the balloons at vascular bifurcation. A stent can be crimped onto the balloons such that inflation of the balloons implants the stent within the bifurcation.

17 Claims, 16 Drawing Sheets

U.S. PATENT DOCUMENTS

| | | | |
|---|---|---|---|
| 6,129,738 A * | 10/2000 | Lashinski et al. | 606/194 |
| 6,142,973 A | 11/2000 | Carleton et al. | |
| 6,165,195 A | 12/2000 | Wilson et al. | |
| 6,210,380 B1 | 4/2001 | Mauch | |
| 6,210,429 B1 | 4/2001 | Vardi et al. | |
| 6,221,098 B1 | 4/2001 | Wilson et al. | |
| 6,254,593 B1 | 7/2001 | Wilson | |
| 6,258,073 B1 | 7/2001 | Mauch | |
| 6,258,116 B1 | 7/2001 | Hojeibane | |
| 6,264,682 B1 | 7/2001 | Wilson et al. | |
| 6,346,089 B1 | 2/2002 | Dibie | |
| 6,361,544 B1 | 3/2002 | Wilson et al. | |
| 6,371,978 B1 | 4/2002 | Wilson | |
| 6,383,213 B2 | 5/2002 | Wilson et al. | |
| 6,387,120 B2 | 5/2002 | Wilson et al. | |
| 6,406,489 B1 | 6/2002 | Richter et al. | |
| 6,428,567 B2 | 8/2002 | Wilson et al. | |
| 6,436,104 B2 | 8/2002 | Hojeibane | |
| 6,475,208 B2 | 11/2002 | Mauch | |
| 6,494,875 B1 | 12/2002 | Mauch | |
| 6,508,836 B2 | 1/2003 | Wilson et al. | |
| 6,520,988 B1 | 2/2003 | Colombo et al. | |
| 6,540,779 B2 | 4/2003 | Richter et al. | |
| 6,544,219 B2 | 4/2003 | Happ et al. | |
| 6,579,312 B2 | 6/2003 | Wilson et al. | |
| 6,582,394 B1 | 6/2003 | Reiss et al. | |
| 6,599,316 B2 | 7/2003 | Vardi et al. | |
| 6,673,107 B1 | 1/2004 | Brandt et al. | |
| 6,695,877 B2 | 2/2004 | Brucker et al. | |
| 6,706,062 B2 | 3/2004 | Vardi et al. | |
| 6,709,440 B2 | 3/2004 | Callol et al. | |
| 6,746,476 B1 | 6/2004 | Hojeibane | |
| 6,749,628 B1 | 6/2004 | Callol et al. | |
| 6,770,091 B2 | 8/2004 | Richter et al. | |
| 6,770,092 B2 | 8/2004 | Richter | |
| 6,780,174 B2 | 8/2004 | Mauch | |
| 6,802,856 B2 | 10/2004 | Wilson | |
| 6,875,229 B2 | 4/2005 | Wilson et al. | |
| 6,887,258 B2 | 5/2005 | Denison et al. | |
| 6,896,699 B2 | 5/2005 | Wilson et al. | |
| 6,955,687 B2 | 10/2005 | Richter et al. | |
| 6,955,688 B2 | 10/2005 | Wilson et al. | |
| 7,018,400 B2 | 3/2006 | Lashinski et al. | |
| 7,090,694 B1 | 8/2006 | Morris et al. | |
| 7,105,019 B2 | 9/2006 | Hojeibane | |
| 7,118,593 B2 | 10/2006 | Davidson et al. | |
| 7,208,001 B2 * | 4/2007 | Coyle et al. | 606/194 |
| 7,220,275 B2 | 5/2007 | Davidson et al. | |
| 7,273,486 B2 * | 9/2007 | Coyle et al. | 606/194 |
| 7,341,598 B2 | 3/2008 | Davidson et al. | |
| 7,445,610 B2 | 11/2008 | Adams et al. | |
| 7,465,315 B2 | 12/2008 | Morris et al. | |
| 7,481,837 B2 | 1/2009 | Wilson | |
| 7,491,228 B2 | 2/2009 | Doran et al. | |
| 7,537,609 B2 | 5/2009 | Davidson et al. | |
| 7,572,272 B2 | 8/2009 | Denison et al. | |
| 7,578,841 B2 | 8/2009 | Yadin et al. | |
| 7,604,621 B2 | 10/2009 | Eidenschink | |
| 7,641,685 B2 | 1/2010 | Richter | |
| 7,708,772 B2 | 5/2010 | Wilson et al. | |
| 7,753,950 B2 | 7/2010 | Wilson et al. | |
| 7,766,955 B2 | 8/2010 | Vardi et al. | |
| 7,815,675 B2 | 10/2010 | Davidson et al. | |
| 7,842,077 B2 | 11/2010 | Hojeibane | |
| 7,850,725 B2 | 12/2010 | Vardi et al. | |
| 7,875,071 B2 | 1/2011 | Richter | |
| 7,892,279 B2 | 2/2011 | Davidson et al. | |
| 7,951,192 B2 | 5/2011 | Yadin et al. | |
| 7,955,379 B2 | 6/2011 | Wilson et al. | |
| 7,959,667 B2 | 6/2011 | Ta et al. | |
| 8,088,102 B2 | 1/2012 | Adams et al. | |
| 2002/0077591 A1 | 6/2002 | Happ et al. | |
| 2003/0055483 A1 | 3/2003 | Gumm | |
| 2003/0093109 A1 | 5/2003 | Mauch | |
| 2004/0098114 A1 | 5/2004 | Wilson et al. | |
| 2004/0176837 A1 | 9/2004 | Atladottir et al. | |
| 2004/0220606 A1 * | 11/2004 | Goshgarian | 606/194 |
| 2005/0038494 A1 | 2/2005 | Eidenschink | |
| 2005/0055012 A1 * | 3/2005 | Trerotola | 604/508 |
| 2005/0080452 A1 * | 4/2005 | Akerfeldt | 606/213 |
| 2005/0085845 A1 | 4/2005 | Hilaire et al. | |
| 2006/0259116 A1 | 11/2006 | Feld et al. | |
| 2006/0271152 A1 | 11/2006 | Hilaire et al. | |
| 2006/0282154 A1 | 12/2006 | Oepen et al. | |
| 2006/0287703 A1 | 12/2006 | Oepen et al. | |
| 2007/0142819 A1 * | 6/2007 | El-Nounou et al. | 604/509 |
| 2007/0173920 A1 * | 7/2007 | Eidenschink | 623/1.11 |
| 2007/0288082 A1 * | 12/2007 | Williams | 623/1.11 |
| 2008/0051705 A1 * | 2/2008 | Von Oepen et al. | 604/101.01 |

FOREIGN PATENT DOCUMENTS

| | | |
|---|---|---|
| EP | 0 897 700 | 2/1999 |
| EP | 1182989 | 1/2004 |
| EP | 956832 | 6/2005 |
| EP | 1040795 | 7/2005 |
| EP | 1157674 | 7/2005 |
| EP | 804907 | 11/2005 |
| EP | 944366 | 9/2006 |
| EP | 1512380 | 8/2007 |
| EP | 1047356 | 9/2008 |
| EP | 1643937 | 4/2009 |
| EP | 1857082 | 12/2009 |
| WO | WO 96/34580 | 11/1996 |
| WO | WO 02/09618 | 2/2002 |
| WO | WO 03/045464 | 6/2003 |
| WO | WO 2006127920 | 11/2006 |
| WO | WO 2007/103553 | 9/2007 |

* cited by examiner

CATHETER SYSTEM AND METHOD FOR DELIVERING MEDICAL DEVICES

This application claims the benefit of U.S. Provisional Application No. 60/823,351, filed Aug. 23, 2006, the entire disclosure of which is incorporated by reference herein.

BACKGROUND OF THE INVENTION

1. Field of the Invention

The present invention relates generally to treatments of vascular disease and, more particularly, to systems and methods for delivering stents to a bifurcated vessel.

2. Description of the State of the Art

The use of medical devices for treating medical conditions in patients is well known. In particular, medical devices are commonly used during the treatment of vascular conditions involving lesions that block or restrict blood flow within body vessels. These procedures usually require that the medical devices be delivered to the treatment site by accessing and tracking through the vessel system.

For example, in a medical procedure known as percutaneous transluminal coronary angioplasty (PTCA), a balloon catheter is used to treat a coronary artery (or other vessel), which has become narrowed or restricted due to the accumulation of plaque along the artery wall. In the PTCA procedure, a balloon catheter is inserted percutaneously and is advanced through the lumen of the coronary artery to the site of a stenosis or blockage. The balloon is then inflated to press the plaque against the artery wall thereby dilating the lumen of the artery and establishing adequate blood flow.

After the PTCA procedure has been performed, a stent may be deployed to prevent restenosis at the treatment site and maintain a clear pathway for the flow of blood. A balloon catheter with an expandable stent mounted over the balloon is advanced through the lumen until the stent is in the desired location. The balloon is then temporarily inflated, thereby expanding and implanting the stent in the vessel. The balloon is then deflated and the balloon catheter assembly is removed from the lumen, leaving the expanded and implanted stent in the vessel to support the vessel wall and prevent development of restenosis.

Although most diseased arteries can be successfully treated in this manner using conventional balloon catheters and stents, arteries that are diseased at a bifurcation are difficult to treat with the devices currently available. For example, when a conventional balloon catheter is used to treat one of the vessel passages at a bifurcation during PTCA, the pressure from the expansion of the balloon in the treated passage can restrict the flow of blood to the untreated passage by pushing the carina over the ostium of the untreated vessel. In addition, the pressure of the balloon in the treated passage may shift the plaque from the treated passage to the untreated passage. If sufficient plaque is shifted to the untreated passage, the ostium of the untreated passage can become so occluded that it becomes difficult or impossible to insert a guidewire and catheter to perform a PTCA in the untreated vessel.

Effectively deploying a stent at a bifurcation is also very challenging. Conventional stents are designed to repair areas of blood vessels that are removed from bifurcations and, since a conventional stent generally terminates at right angles to its longitudinal axis, the use of conventional stents in the region of a vessel bifurcation may result in blocking blood flow of a side branch (commonly referred to as "jailing" the side branch) or fail to repair the bifurcation to the fullest extent necessary. To be effective, the stent must overlay the entire circumference of the ostium to a diseased portion and extend to a point within and beyond the diseased portion. Where the stent does not overlay the entire circumference of the ostium to the diseased portion, the stent fails to completely repair the bifurcated vessel. In this case, the stent also acts as a barrier to passing a secondary balloon catheter or stent delivery system, thereby further complicating and increasing the risk of a failed procedure.

To overcome the problems and limitations associated with the use of conventional stents, a Y-shaped stent has been proposed for the treatment of bifurcations. Such a stent has the advantage of completely repairing the vessel at the bifurcation without obstructing blood flow in the other portions of the bifurcation. In addition, such a stent allows access to all portions of the bifurcated vessel should further interventional treatment be necessary. In a situation involving disease in the origin of an angulated aorta-ostial vessel, such a stent would have the advantage of completely repairing the vessel origin without protruding into the aorta or complicating repeat access. The proposed Y-shaped stent provides an improved device for repairing bifurcations. However, the delivery and deployment of such a stent cannot be easily accomplished with a conventional balloon catheter.

Because a conventional balloon catheter is not adequate for treating an arterial bifurcation, many physicians currently employ a "kissing balloon" technique in which two separate balloon catheters are inserted into a guide catheter and each balloon tracks over a separate guidewire. The guide catheter is advanced to a point proximal to the bifurcation site and two guidewires are then advanced from the distal end of the guide catheter into separate vessel passages. The two balloon catheters then track over the guidewires into the respective passages. The balloons are simultaneously inflated using either separate inflation media or from a single source using a manifold which divides the flow. The two catheters are used together for PTCA or stenting so that both vessel passages at a bifurcation site can be treated simultaneously.

Although generally effective, the use of two single balloon catheters to treat arterial bifurcations has significant drawbacks. For example, the presence of two similar catheters exiting the proximal end of the guide catheter makes it difficult for a physician to manage both devices without becoming confused as to which catheter controls a particular balloon. Furthermore, the presence of two balloon catheters within one guide catheter creates a large device profile thereby limiting the amount of radiopaque dye, which can be injected into the vessel to allow the physician to view the bifurcation. Additionally, the profile of the combined balloon catheters may require the physician to use a larger guide catheter than preferred. Further still, a system with two separate balloon catheters has increased stiffness in the proximal system region, resulting in deliverability difficulties.

Many of the existing concepts for bifurcation stent delivery systems include a single catheter shaft that branches into separate catheter shaft branches having associated balloons. The aim of these systems is to overcome the drawbacks of using two separate balloon catheters, as previously discussed. While reasonably effective, these systems also include drawbacks of their own. For example, these systems generally must track over two guidewires that are initially placed within the branches of the bifurcated vessel. Since each guidewire is potentially twisted around the other, there may be significant resistance to deliverability of the catheter system to the disease location. Additionally, since the proximal catheter body is usually attached to the distal catheter branches through the use of a connection of some nature, the stiffness and profile of the system is increased at the connection locale. This can cause further difficulties in tracking to the disease location as mentioned earlier.

Efforts have been made to develop a balloon catheter that is designed specifically for the treatment of arterial bifurcation. Such efforts have led to the proposal of a Y-shaped balloon disposed at the distal end of a catheter that is inflated in a bifurcation to treat both passages simultaneously. Although a Y-shaped balloon would provide an improvement over the use of two separate balloon catheters, the proposed device may not be practical due to challenges of manufacturing a Y-shaped balloon, attaching it to a catheter shaft, and properly positioning it at a bifurcated blood vessel.

The present invention provides a stent delivery system for the treatment of bifurcated vessel disease that seeks to overcome the downfalls of the prior art. This is achieved by the advantageous aspects of the invention. For example, as a result of the system design, a stent can be deployed at a bifurcation in a way that provides complete coverage of the ostium circumference. Deliverability of the stent to the bifurcation is also improved, since the system incorporates features to reduce profile and improve system flexibility. Further still, at least one embodiment of the system provides the advantage of delivering the system to the bifurcation over a single guidewire, thereby reducing the risk of encountering guidewire wrapping that hinders stent deliverability.

SUMMARY OF THE INVENTION

Briefly and in general terms, the present invention is directed to medical device delivery systems and methods. A medical device delivery system comprises a first shaft including a proximal segment, a distal segment narrower than the proximal segment, and a transition portion disposed between the proximal and distal segments, a second shaft attached to the first shaft at a location about the transition portion, a first balloon on the distal segment of the first shaft, and a second balloon on the second shaft.

In aspects of the present invention, the system further comprises a first guidewire lumen associated with the first balloon, a second guidewire lumen associated with the second balloon, and a third guidewire lumen removably coupled to the first shaft, the third guidewire lumen in communication with the second guidewire lumen.

In further aspects, the third guidewire lumen is removably coupled to the first shaft by a coupling device including a first tubular wall defining a guidewire passageway, a second tubular wall sized to receive the first shaft, and an axially extending opening formed through at least a portion of the second tubular wall.

The medical device delivery system, in other aspects of the invention, further comprises an anchor member attached to either one of the first and second balloons and an anchor housing attached to the other one of the first and second balloons, the anchor housing having a recess sized to receive the anchor member such that the anchor member is removably retained within the anchor housing.

In other aspects of the present invention, a medical device delivery system comprises a proximal shaft, a first distal shaft attached to the proximal shaft, the first distal shaft narrower than the proximal shaft, a second distal shaft attached to either one of the proximal shaft and the first distal shaft, a first balloon adjacent a distal end of the first distal shaft, a second balloon adjacent a distal end of the second distal shaft, and a coupling device that connects the distal ends of the first and second shafts together.

In further aspects, the coupling device couples the distal end of the second shaft to a first guidewire and the coupling device is configured to allow the distal end of the second shaft to disconnect from the first guidewire after advancement of a second guidewire into the coupling device. In detailed aspects, the coupling device couples the distal end of the second shaft to a first guidewire and the coupling device is configured to allow the distal end of the second shaft to separate from the first guidewire after application of a force to the coupling device.

In still further aspects, the medical device delivery system comprises a first guidewire lumen extending through the first distal shaft, a second guidewire lumen extending through the second distal shaft, and a third guidewire lumen removably coupled to the proximal shaft, the third guidewire lumen in communication with the second guidewire lumen.

A method of delivering a medical device, in other aspects of the invention, comprises coupling a removable guidewire lumen to a catheter including a first shaft, a second shaft attached to the first shaft, a first guidewire lumen associated with a first balloon, and a second guidewire lumen associated with a second balloon, the first guidewire lumen extending through the first shaft having a proximal portion and a distal portion narrower than the proximal portion, the second guidewire lumen extending through the second shaft.

In further aspects, the removable guidewire lumen is coupled to the catheter by a coupling device including a tubular wall retaining the first shaft and defining a guidewire passageway, and wherein an axially extending opening is formed through at least a portion of the tubular wall.

In other aspects, the method further comprises coupling distal ends of the first and second balloons together. In detailed aspects, one of the first and second balloons is attached to an anchor member and the other of the first and second balloons is attached to an anchor housing having a recess configured to retain the anchor member in manner such that a force applied to either one or both of the anchor member and the anchor housing causes the anchor member to be released from the anchor housing. In other detailed aspects, one of the first and second balloons is attached to a suture and the other of the first and second balloons is attached to a distal tip to which the suture is removably attached such that a force applied to either one or both of the suture and the distal tip causes the suture to be released from the distal tip.

In further detailed aspects, one of the first and second balloons is attached to an insertion member and the other one of the first and second balloons is attached to a housing member having a tubular wall and a slit formed through the tubular wall, the tubular wall configured to retain the insertion member, the tubular wall defining an end portion of a guidewire passageway, and the tubular wall configured to release the insertion member when a guidewire is advanced within the end portion of the guidewire passageway. In other detailed aspects, either one of the first and second balloons is attached to a distal tip including a wall configured to retain a first guidewire associated with the other of the first and second balloons, the wall of the distal tip defining an end portion of a guidewire passageway, and the wall is configured to release the first guidewire when a second guidewire is advanced within the end portion of the guidewire passageway.

The features and advantages of the invention will be more readily understood from the following detailed description which should be read in conjunction with the accompanying drawings.

DETAILED DESCRIPTION OF THE INVENTION

Figure 1A:
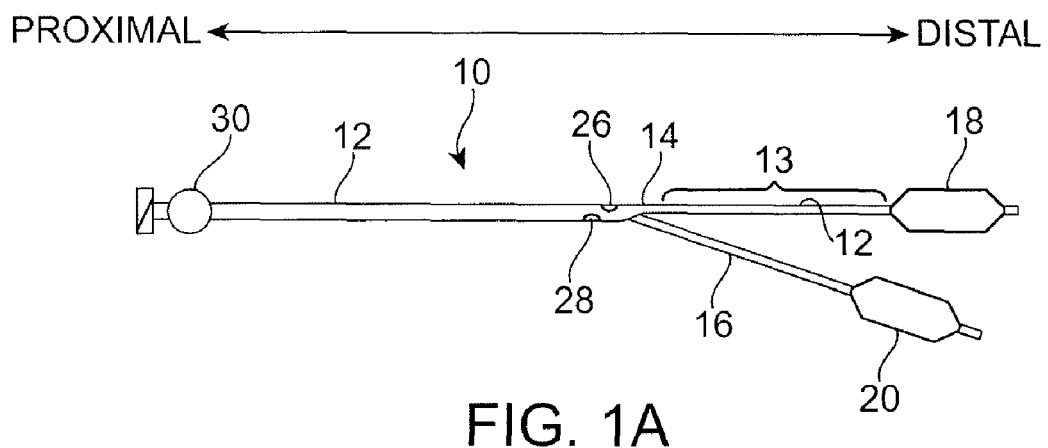
FIGS. 1A-1C show a stent delivery system in accordance with embodiments of the present invention.

The present invention enjoys several advantages over the prior art. For example, embodiments of a medical device delivery system design and construction permit increased flexibility and reduced cross-sectional profile, which facilitate placement of a stent at the desired anatomical location. Embodiments of medical device delivery systems and methods allow a stent to be easily and effectively deployed at the ostium of a bifurcated vessel. These and other advantages will be more readily understood from the following detailed description.

Briefly, in an exemplary embodiment of the invention, a medical device delivery system can include first and second elongated shafts, the second elongated shaft extending from the first elongated shaft at a predetermined location. The delivery system is used to deliver a medical device to an anatomical site. The medical device can be an angioplasty balloon, a stent, a graft, another implantable device, or combinations thereof.

Each elongated shaft can have a balloon disposed near the distal end, the balloons being in fluid communication with an inflation lumen disposed within the elongated shaft. A stent or other implantable device can be radially disposed about the balloons, and expansion of the balloons causes deployment and implantation of the stent or other medical device.

A first guidewire lumen can extend along the length of the first elongated shaft, and a second guidewire lumen can extend along the length of the second elongated shaft. The second guidewire lumen can terminate in a proximal aperture or opening disposed on either the first or second elongated shaft.

The stent delivery system can include a removable guidewire lumen that communicates with the proximal opening of the second guidewire lumen. The removable guidewire lumen includes a coupling feature that is defined by a wall discontinuity in the removable guidewire lumen.

The stent delivery system can also include a first catheter tip adjacent the distal end of the first elongated shaft and a second catheter tip adjacent the distal end of the second elongated shaft. An anchor housing feature can be defined by a passage within the first catheter tip. An anchor element can be disposed within the second catheter tip, and the anchor element can engage the anchor housing, thereby associating the first catheter tip with the second catheter tip.

A slit may be formed adjacent the distal end of the second catheter tip. The first catheter tip can be passed through the slit, thereby radially disposing the second catheter tip about the first catheter tip over a portion of the slit length. The second catheter tip can be radially disposed about a guidewire over a portion of the slit length.

A method of delivering balloons or other medical device to a bifurcation, in accordance with an embodiment of the present invention, involves placement of separate guidewires in each branch of a bifurcated vessel. A medical device delivery system, such as briefly described above, can be tracked over the guidewires to the bifurcation. Once the delivery system has been tracked to the bifurcated vessel, the first and second balloons can be expanded. Optionally and not necessarily, there can be a stent or other implantable device on the balloons such that the stent is deployed in the bifurcation when the balloons are expanded.

In another method, a first guidewire is placed in a first branch of a bifurcated vessel. A delivery system, such as briefly described above, can be tracked over the first guidewire to a location proximal to the bifurcation. A second guidewire can be tracked through a removable guidewire lumen and a second elongated shaft of the delivery system and into a second branch of the bifurcated vessel. Optionally and not necessarily, prior to tracking the second guidewire through the removable guidewire lumen, an anchor element associated with the second balloon can be disengaged from the anchor housing associated with the first balloon, thereby disconnecting the catheter tips of the balloons.

The delivery system can be tracked over the guidewires, to the bifurcated vessel location. Once the delivery system has been tracked to the bifurcated vessel, the first and second balloons can be expanded. Optionally and not necessarily, there can be a stent or other medical device on the balloons such that the stent or other medical device is implanted in the bifurcation when the balloons are expanded.

Figure 1B:
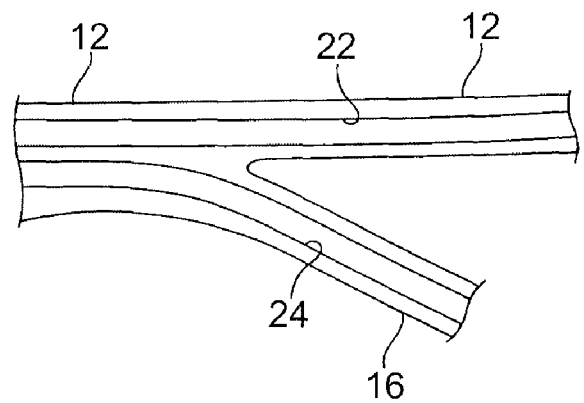
Figure 1C:
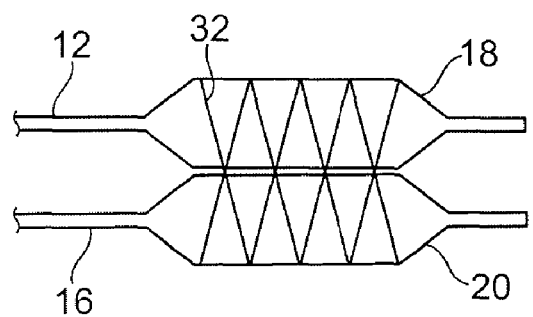

Referring now in more detail to the exemplary drawings for purposes of illustrating embodiments of the invention, wherein like reference numerals designate corresponding or like elements among the several views, there is shown in FIGS. 1A-1C a stent delivery system 10 that can be used for the treatment of vascular disease including the treatment of disease within bifurcated vessels.

In FIG. 1A, the stent delivery system 10 includes a first elongated shaft 12 with a distal end and a proximal end. The first elongated shaft 12 reduces in diameter over a portion 13 of the distal end, beginning at a tapered or necking location 14. The necking location 14 functions as a transition between the wider proximal portion and the narrower distal portion of the first elongated shaft 12. The system 10 further includes a second elongated shaft 16, which branches from the first elongated shaft 12 at a location adjacent to the necking location 14. The second elongated shaft 16 includes a distal and a proximal end. The reduced diameter portion 13 of the first shaft 12 is adjacent the second shaft 16. This configuration has the advantage of reducing the cross-sectional profile of the system 10 to facilitate introduction and positioning of the system within an anatomical lumen.

An inflation lumen is disposed within the first elongated shaft 12 and is in fluid communication with a luer 30 adjacent the proximal end of the first elongated shaft 12. In this embodiment, the term lumen refers to an interior space of a tubular structure or to a tubular structure that defines an interior space. A first balloon 18 is disposed about the first elongated shaft 12 adjacent the distal end of the shaft 12. A second balloon 20 is disposed about the second elongated shaft 16 adjacent the distal end of the second shaft 16. The inflation lumen is in fluid communication with the first and second balloons 18, 20 and allows for expansion and contraction of the balloons.

FIG. 1B shows a detail view of a portion of the stent delivery system 10 of FIG. 1A near the necking location 14. The stent delivery system 10 includes at least two guidewire lumens 22, 24 extending through the first and second shafts 12, 16. A first guidewire lumen 22 is at least partially defined by tubular walls of the first elongated shaft 12. The first guidewire lumen 22 has a distal opening adjacent the distal end of the first elongated shaft 12 and a proximal opening 26 (FIG. 1A) at a location proximal to the first balloon 18.

Referring again to FIGS. 1A and 1B, the first guidewire proximal opening 22 is shown adjacent to the necking location 14. This configuration results in a rapid-exchange type of guidewire lumen through the first shaft 12. A second guidewire lumen 24 is at least partially defined by tubular walls of the first and second elongated shafts 12, 16. The second guidewire lumen 24 has a distal opening adjacent the distal end of the second elongated shaft 16 and a proximal opening 28 at a location proximal to the second balloon 20. The second guidewire lumen proximal opening 28 is shown adjacent the necking location 14. This configuration provides for a rapid-exchange type guidewire lumen through the second shaft 16.

Referring now to FIG. 1C, a stent 32 can be disposed about the first balloon 18 and second balloon 20. As is well known in the art, the stent 32 may be fabricated from a variety of materials, such as polymers, stainless steel, cobalt chromium, Nitinol, and other metals and alloys, through the use of various manufacturing procedures, such as laser cutting, photo-etching, mechanical machining, descaling, electropolishing, and other processes. Prior to inserting the delivery system 10 into an anatomical lumen, such as a blood vessel, the stent 32 is crimped to a small diameter over the balloons 18, 20 while the balloons are in an uninflated or folded state. When the stent 32 has been positioned and oriented within a target location, such as the ostium of a bifurcated vessel, the stent can be deployed by inflation and expansion of the balloons.

Figure 2:
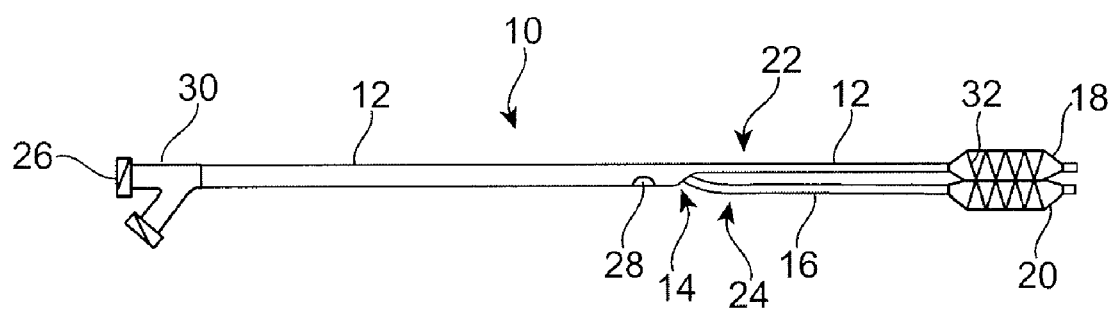
FIG. 2 is a side elevation view of a stent delivery system, the view showing an over-the-wire type of guidewire lumen associated with a first balloon and a rapid-exchange type of guidewire lumen associated with a second balloon.

In FIG. 2, a stent delivery system 10 in accordance with an embodiment of the present invention includes a first guidewire lumen proximal opening 26 adjacent the proximal end of the first elongated shaft 12. This configuration provides an over-the-wire type of guidewire lumen through the first elongated shaft 12. A second guidewire lumen proximal opening 28 is adjacent to a necking location 14. This configuration provides a rapid-exchange type of guidewire lumen through the second elongated shaft 16.

In other embodiments, a stent delivery system 10 may include an over-the-wire type of guidewire lumen through the second shaft 16, or any other combination of guidewire lumen exchange types.

Figure 3A:
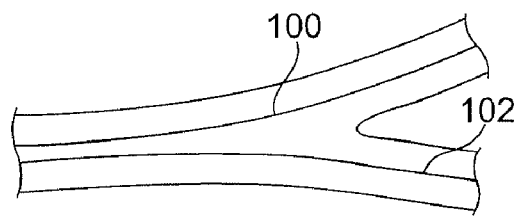
FIGS. 3A-3D illustrate a method of delivering a stent to a bifurcated vessel, the method involving guiding a stent delivery system to a bifurcation using two guidewires.

Referring now to FIGS. 3A-3D, a method is provided for deploying a stent within a bifurcated vessel using a stent delivery system 10. In FIG. 3A, a first guidewire 100 is placed within a first branch of the bifurcated vessel and a second guidewire 102 is placed within a second branch of the bifurcated vessel.

Figure 3B:
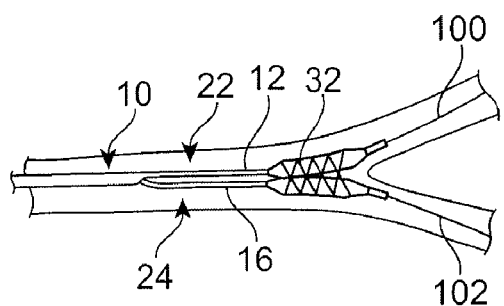

As shown in FIG. 3B, the first guidewire 100 can be inserted within the first guidewire lumen 22 and the second guidewire 102 can be inserted within the second guidewire lumen 24. The stent delivery system 10 can be advanced over the first and second guidewires to the ostium of a bifurcated vessel. The stent 32, which is disposed about the first and second balloons, can be brought into contact with the carina of the bifurcation, thereby ensuring effective scaffolding of the ostium circumference.

Figure 3C:
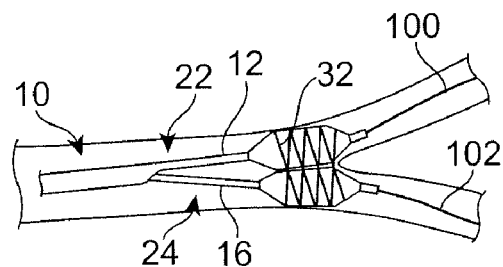
Figure 4:
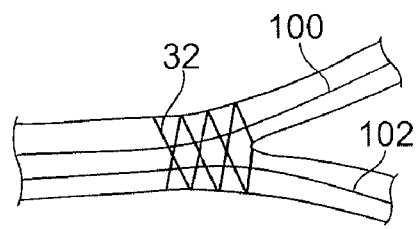
FIG. 4 shows a stent delivered to a bifurcated vessel and first and second guidewires left in place within the bifurcated vessel after a stent delivery system has been removed from the bifurcated vessel.

In FIG. 3C, fluid is introduced via a luer and into an inflation lumen in fluid communication with first and second balloons 18, 20. Fluid introduced into the luer 30 is delivered to the first and second balloons 18, 20. Introduction of fluid results in the inflation and expansion of the balloons 18, 20, which expands and deploys the stent 32 at a location within the bifurcated vessel or other anatomical location, such as shown in FIG. 4.

Figure 3D:
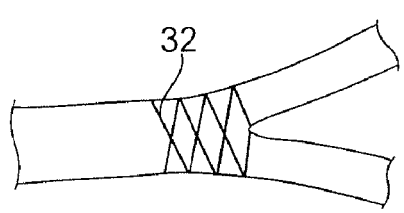

In FIG. 3D, fluid has been removed via the luer from the inflation lumen such that the balloons 18, 20 deflate and contract in size. The stent delivery system 10 and guidewires 100, 102 have been removed from the anatomy, leaving the deployed stent 32 in place. Alternatively, the guidewires 100, 102 may be left within the anatomy to facilitate subsequent treatment of the bifurcation with another device.

In FIG. 5, there is shown a stent delivery system 10 in accordance with another embodiment of the present invention. The system 10 includes a removable guidewire lumen 40. The removable guidewire lumen 40 has a distal end 41, a proximal end 42, and an elongated member 43 disposed between the two ends 41, 42. Adjacent the distal end 41 is an engaging lumen 50. In the illustrated embodiment, the engaging lumen 50 has an outer diameter sized for insertion within a second guidewire lumen proximal opening 28. The engaging lumen 50 has an inside diameter sized to receive a guidewire, thereby allowing a guidewire to be passed through the removable guidewire lumen 40 and the second guidewire lumen 24 within the second shaft 16.

Figure 5A:
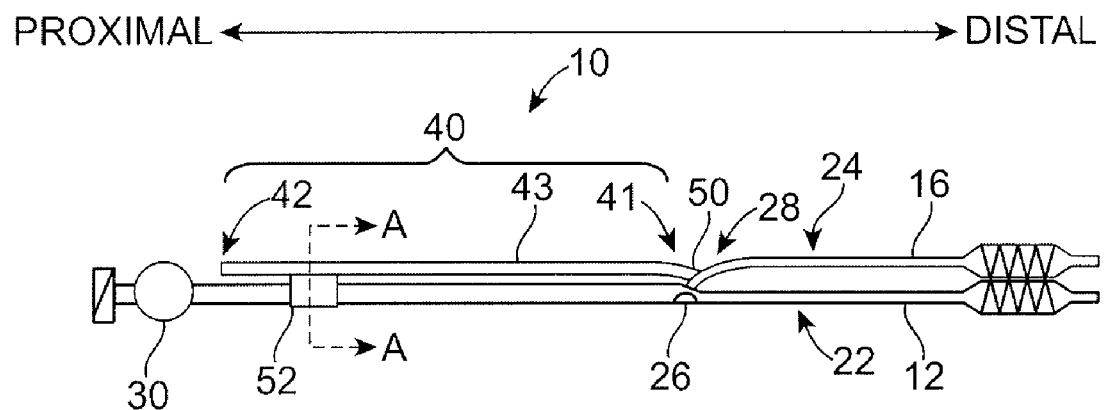
FIG. 5A is a side elevation view of a stent delivery system, the view showing a coupling device for removably attaching a removable guidewire lumen to a first catheter shaft.
Figure 5B:
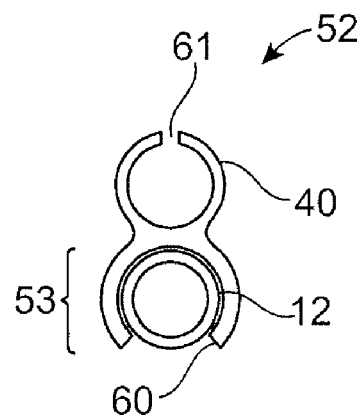
FIG. 5B is a cross-sectional view of the coupling device of FIG. 5A showing a tubular wall having a first portion defining a guidewire passageway and a second portion holding the first catheter shaft containing an inflation lumen.

Referring to FIGS. 5A and 5B, the system 10 further includes a coupling feature 52. The coupling feature 52 can be formed as part of the overall removable guidewire lumen 40 structure. Alternatively, it may be fabricated separately from the removable guidewire lumen 40 and later associated with the removable guidewire lumen. This association may be accomplished through the use thermal welding, adhesive bonding, and processes well known in the art.

As shown in FIG. 5B, the coupling feature 52 includes generally C-shaped cross-sectional geometry 53 defined by a lumen with a wall discontinuity 60. FIG. 5B shows a cross-sectional view of the system 10 taken about line A-A in FIG. 5A. The first elongated shaft 12 can be passed through the wall discontinuity 60, thereby connectively associating it with the removable guidewire lumen 40.

Still referring to FIG. 5B, there is an axial guidewire slit 61 formed along at least a portion of the removable guidewire lumen 40. A guidewire inserted within the removable guidewire lumen 40 can be passed through the guidewire slit 61 to remove the guidewire from the removable guidewire lumen 40.

Figure 6A:
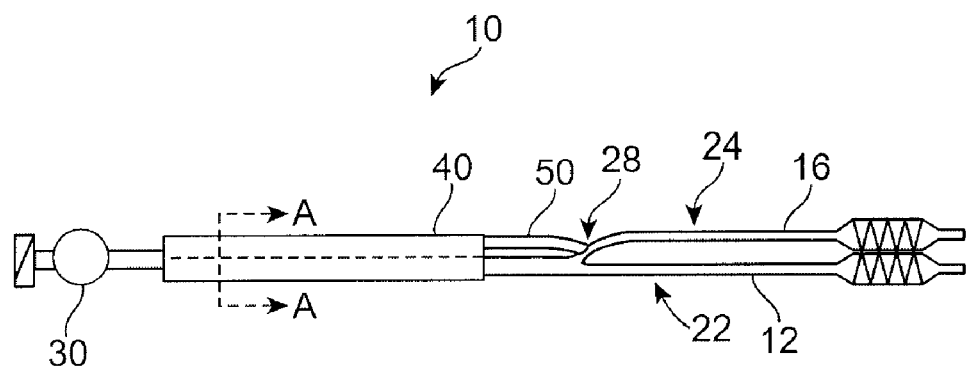
FIGS. 6A-6C illustrate a stent delivery system in accordance with embodiments of the present invention and shows a first shaft defining a first guidewire passageway associated with a first balloon, a coupling device carrying the first shaft, a second shaft attached to the first shaft, a removable lumen disposed between the coupling device and the second shaft, wherein the coupling device, the removable lumen, and the second shaft define a second guidewire passageway associated with a second balloon.

In FIG. 6A, there is shown a stent delivery system 10 in accordance with an embodiment of the present invention, wherein a removable guidewire lumen 40 is coupled over a substantial axial length of a first elongated shaft 12. In the illustrated embodiment, at least half of the entire length of the first shaft 12 is removably coupled to the removable guidewire lumen 40.

Figure 6B:
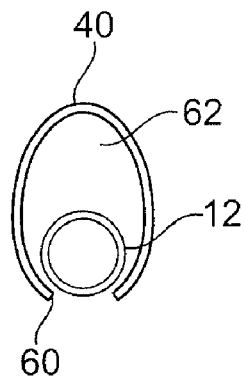

FIG. 6B shows a cross-sectional view of the system 10 taken about line A-A in FIG. 6A. The first elongated shaft 12 has been passed through the wall discontinuity 60 such that it is removably connected to the removable guidewire lumen 40. When the removable guidewire lumen 40 and the first elongated shaft 12 are coupled in this manner, a guidewire space 62 is defined between an interior surface of the guidewire lumen and the first elongated shaft 12. A guidewire can be passed through the guidewire space 62 and into a second guidewire lumen 24.

Figure 6C:
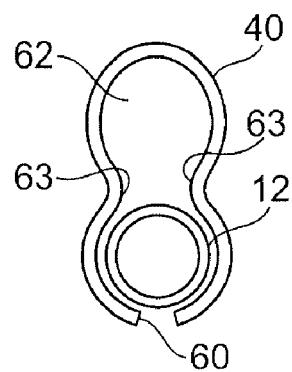

FIG. 6C shows another cross-sectional view taken about line A-A of FIG. 6A. In the illustrated embodiment of FIG. 6C, the cross-section of the removable guidewire lumen 40 is somewhat figure-eight shaped and includes two substantially elliptical sections. One of the elliptical sections including a wall discontinuity 60. A first elongated shaft 12 can be passed through the wall discontinuity 60 in order to removably associate it with the removable guidewire lumen 40. When the removable guidewire lumen 40 and the first elongated shaft 12 are coupled, a guidewire space 62 is defined therebetween. A guidewire can be passed through the guidewire space 62 and into the second guidewire lumen 24. Inwardly protruding portions 63 between the two elliptical sections keep the first shaft 12 from entering the guidewire space 62.

An advantage of the removable guidewire lumen configurations shown in FIGS. 6A-6C is that the removable guidewire lumen 40 can be uncoupled from the first elongated shaft 12 easily, by providing a removal force substantially perpendicular to the central longitudinal axis of the first elongated shaft 12.

Figure 7A:
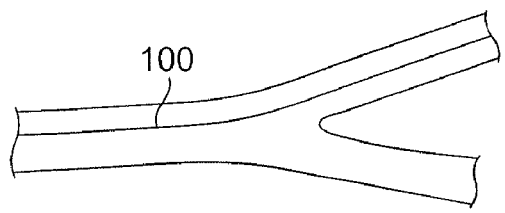
FIGS. 7A-7F show a method of delivering a stent to a bifurcation, the method involving guiding a stent delivery system to a bifurcation using a single guidewire and orienting the stent delivery system at the ostium of the bifurcation using two guidewires.

Referring now to FIGS. 7A-7F, a method is provided for deploying a stent 32 within a bifurcated vessel using a stent delivery system 10 having a removable guidewire lumen 40. In FIG. 7A, a first guidewire 100 is placed within a first branch of the bifurcated vessel.

Figure 7B:
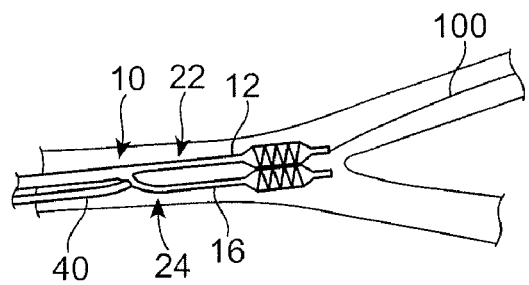

In FIG. 7B, the first guidewire 100 has been inserted within a first guidewire lumen 22. The stent delivery system 10 can be advanced over the first guidewire 100 to the ostium of the bifurcated vessel.

Figure 7C:
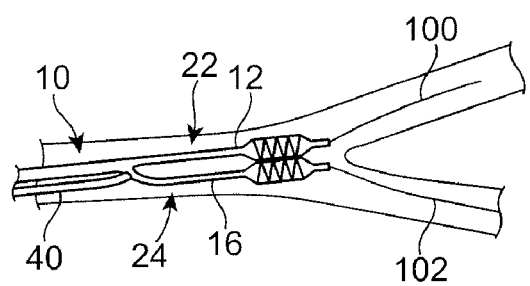

In FIG. 7C, a second guidewire 102 has been inserted within the removable guidewire lumen 40 at the proximal end. The second guidewire 102 can be advanced through the removable guidewire lumen 40 into the second elongated shaft 16 and further into a second branch of the bifurcated vessel.

Figure 7D:
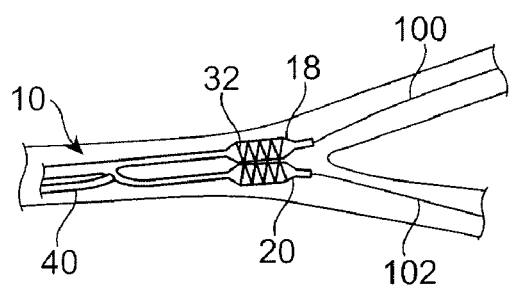

In FIG. 7D, the stent delivery system 10 has been advanced over the first and second guidewires 100, 102 to the ostium of the bifurcated vessel. The stent 32 is disposed about the first and second balloons 18, 20 and is brought into contact with the carina of the bifurcation to ensure effective scaffolding of the ostium circumference.

Figure 7E:
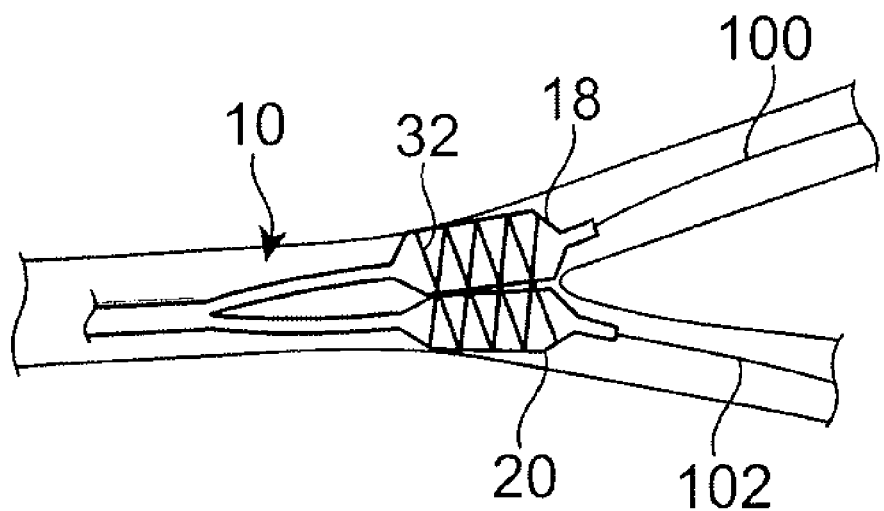

In FIG. 7E, fluid has been introduced via a luer into an inflation lumen that is in fluid communication with the first and second balloons 18, 20. Introduction of fluid inflates and expands the balloons 18, 20, which expands and deploys the stent 32 at a desired location within the bifurcated vessel.

Figure 7F:
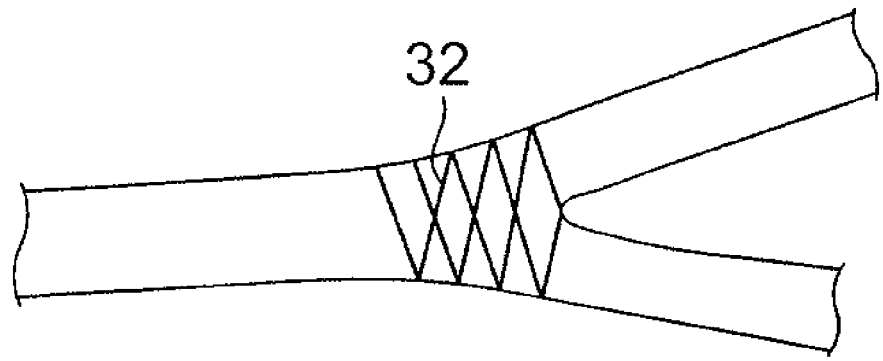

In FIG. 7F, fluid has been removed via the luer from the balloons 18, 20, which reduces the size of the balloons 18, 20 so that the they can be withdrawn away from the deployed stent 32. The stent delivery system 10 and guidewires 100, 102 have been removed from the anatomy, leaving the deployed stent 32 at the bifurcation. Alternatively, the guidewires 100, 102 may be left in the anatomy to facilitate subsequent treatment of the bifurcation with another device.

Figure 8:
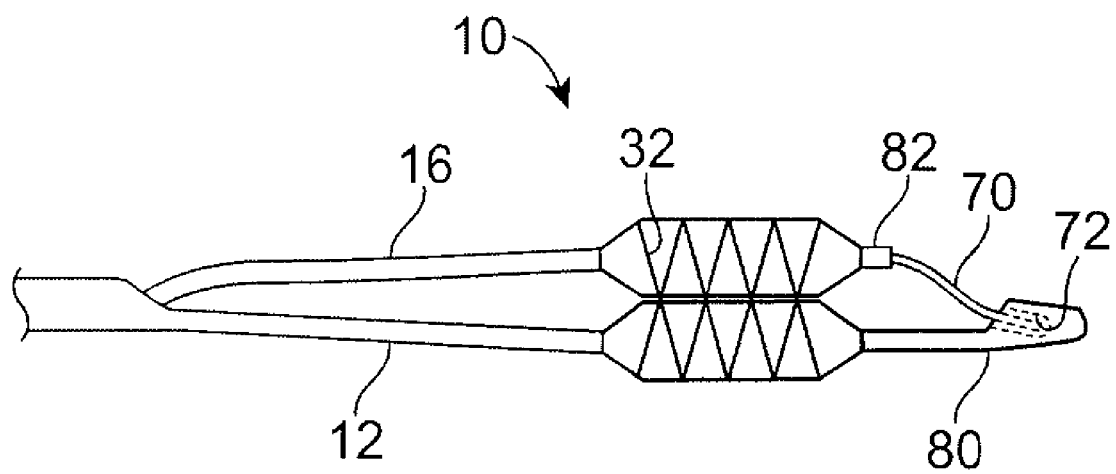
FIG. 8 is a side elevation view of a distal end region of a stent delivery system, the view showing distal ends of first and second balloons connected by means of an anchor member press-fitted within an anchor housing.

FIG. 8 shows a stent delivery system 10 in accordance with an embodiment of the present invention. The system 10 includes a first catheter tip 80 disposed adjacent the distal end of a first elongated shaft 12. An anchor housing 72 is integrally formed on the first catheter tip 80.

Figure 9:
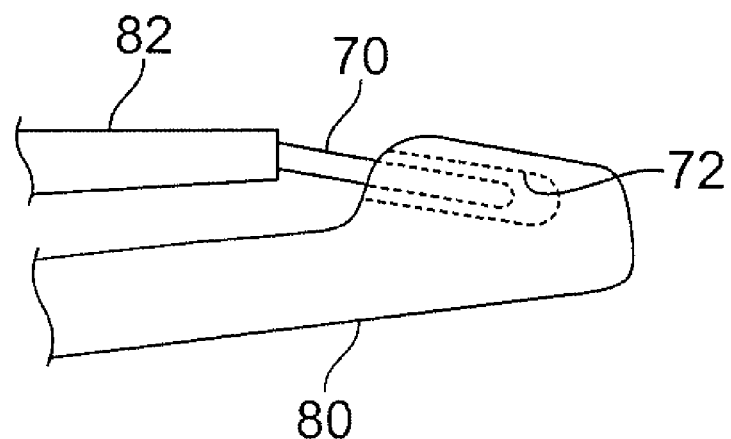
FIG. 9 is a detailed view of the anchor member and the anchor housing of FIG. 8

As shown in FIG. 9, the anchor housing 72 can include a passage, cavity, or recess formed in the first catheter tip 80. The anchor element 70 can be sized to be removably inserted in the anchor housing 72. The anchor element 70 is attached to a second catheter tip 82. The second catheter tip 82 is disposed adjacent the distal end of the second elongated shaft 16. The anchor element 70 removably connects the first and second catheter tips 80, 82 together. This connection provides the advantage of a stent delivery system 10 that can be delivered over a single guidewire, thereby improving the system trackability and mitigating the risk of guidewire entanglement.

Figure 10A:
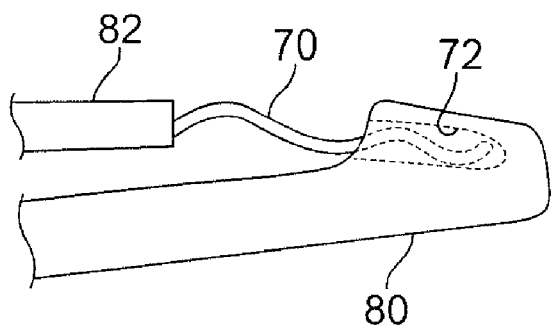
FIGS. 10A-10E are side elevation views illustrating anchor members and anchor housings in accordance with embodiments of the present invention, the anchor members and housings configured to matingly engage one another in order to keep balloon catheter tips together while the balloon catheter is advanced within an anatomical lumen.
Figure 10B:
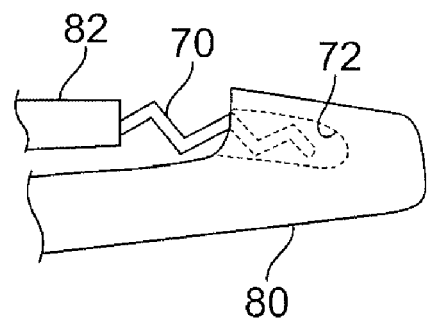

FIGS. 10A-10E show various embodiments of anchor elements. An anchor element 70 may have an undulating shape such as an undulating wave-like shape, as shown in FIG. 10A, or a zig-zag shape, as shown in FIG. 10B. These configurations allow the anchor element 70 to contact an anchor housing 72 surface such that there is a press-fit to secure the anchor element 70 within the anchor housing.

In some embodiments, the wave-like and zig-zag shapes are configured to flex or deform when the anchor element 70 is inserted in the anchor housing 72 and to press against an inner surface of the anchor housing 72. The anchor housing 72 may also deform when the anchor element 70 is inserted. In this manner, the anchor element 70 resists being easily pulled out of the anchor housing 72.

Figure 10C:
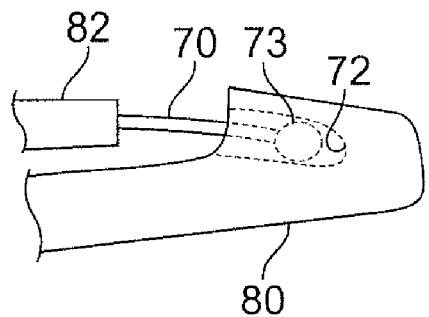

In FIG. 10C, an anchor element 70 has a substantially wire-like structure having a distal end with a bead-like element 73 disposed thereon. The bead-like element 73 creates a press-fit to secure the anchor element 70 within the anchor housing 72.

Figure 10D:
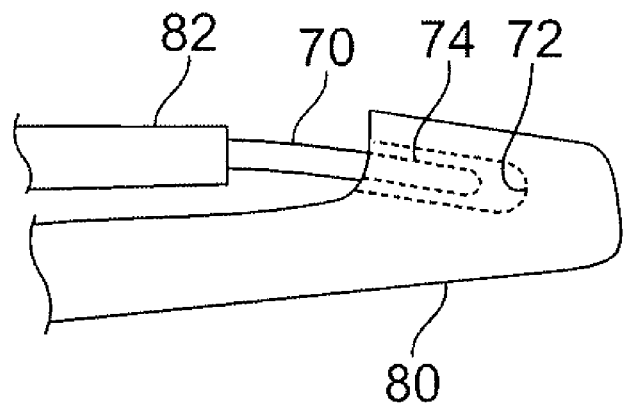

In FIG. 10D, an anchor element 70 has a roughened surface 74. The roughened surface 74 increases friction between the anchor element 70 and an anchor housing 72. In the embodiments of FIGS. 10A-10D, the anchor element 70 is secured within the anchor housing 72 by a press-fit that can be overcome by pulling or applying a tensile load to the anchor element 70. Application of a sufficient tensile load disconnects the first and second catheter tips 80, 82 from each other.

Figure 10E:
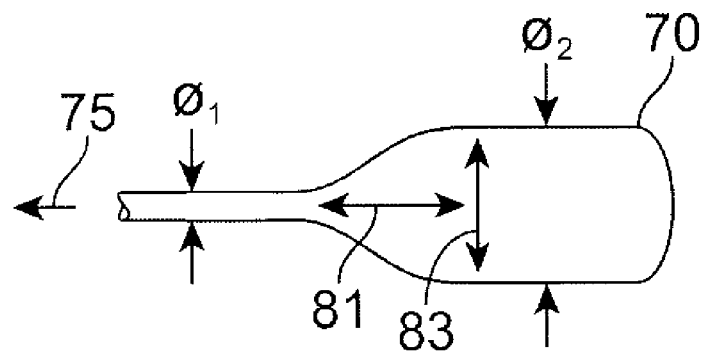

In FIG. 10E, an anchor element 70 is formed of an elastomer, elastomeric material, or resilient material. The anchor element 70 is initially inserted within the anchor housing 72. When inserted, the anchor element outer surface has an interference fit with an anchor housing inner surface. Pulling the anchor element 70 away from the anchor housing 72 or application of a tensile load on the proximal end of the anchor element results in a reduction in an outer diameter and cross-sectional area of the anchor element. The reduction in outer diameter and cross-sectional area occurs as the positive strain along an axial direction 81 results in a negative strain along a radial direction 83. The reduction in outer diameter and cross-sectional area reduces or eliminates the interference fit with the anchor housing 72. Reduction or loss of the interference fit allows the anchor element 70 to pull out of the anchor housing 72, which, in turn, allows the first and second catheter tips 80, 82 to become disconnected from each other.

Figure 11:
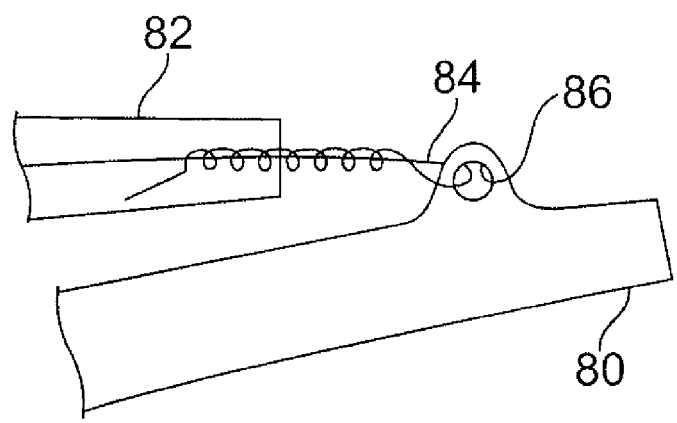
FIG. 11 is a side elevation view of a distal end region of a stent delivery system, the view showing respective catheter tips on first and second balloons connected by means of a suture extending through an eyelet.

In other embodiments of the present invention, an anchor element 70 is formed from a suture-like component, such as a wire, filament, string, thread, or very fine and flexible structure. In FIG. 11, an eyelet feature 86 is formed on a first catheter tip 80. A suture 84 is passed through the eyelet 86 and wrapped or knotted about itself proximal to the eyelet 86. The suture 84 is attached to and disposed within the second catheter tip 82. In this manner, the first and second catheter tips 80, 82 are connectively associated with each other. The first and second catheter tips 80, 82 can be disassociated by applying a sufficient tensile load to the suture 84 such that the wrapping or knot becomes undone and the suture 84 detaches from the eyelet 86. This embodiment provides the advantage of improving the overall system flexibility due to the relatively high flexibility of the suture 84.

In other embodiments, the first catheter tip 80 includes a slit, groove, hook, or a protruding feature which retains the suture 84.

Figure 12:
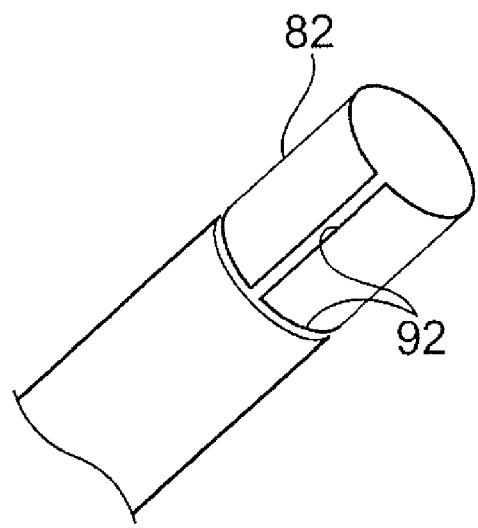
FIG. 12 is a perspective view of a distal end region of a stent delivery system, the view showing a catheter tip of a balloon, the catheter tip having a flexible tubular wall and a slit formed through the tubular wall, the slit extending longitudinally and circumferentially.

In yet another embodiment of a stent delivery system tip configuration, a tip slit can be used. In FIG. 12, a tip slit 92 is located adjacent the distal end of the second catheter tip 82. The slit 92 may be formed after molding the second catheter tip 82, such as by cutting with a razor blade, or during molding of the second catheter tip 82.

Figure 13:
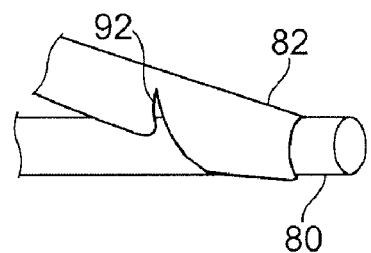
FIG. 13 is a perspective view of a distal end region of a stent delivery system, the view showing an insertion member of a first balloon and a housing member of a second balloon, the housing member having a flexible tubular wall and a slit formed through the tubular wall, a portion of the tubular wall retaining the insertion member.

Referring now to FIG. 13, an embodiment of a tip configuration is shown in which a first catheter tip 80 is passed through the tip slit 92 such that the first catheter tip 80 is nestled within the distal end of the second catheter tip 82. This configuration results in a reduced overall profile and eliminates the need for an additional component to associate the catheter tips 80, 82 and improves overall system stiffness and deliverability.

Figure 14A:
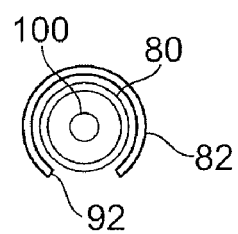
FIGS. 14A-14C are cross-sectional views of a distal end region of a stent delivery system, the views showing a method of retaining distal ends regions of two balloons together and urging the distal end regions to separate through the use of a guidewire.
Figure 14B:
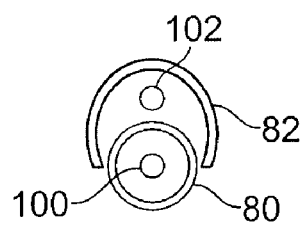
Figure 14C:
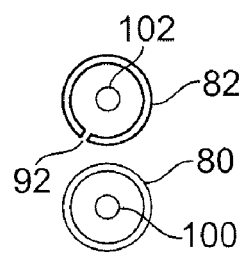

FIGS. 14A-14C show a method of disassociating catheter tips 80, 82 that are associated by means of a tip slit 92. In FIG. 14A, the first catheter tip 80 is disposed about a first guidewire 100, and the second catheter tip 82 is disposed about the first catheter tip 80, such as in the manner shown in FIG. 13. In FIG. 14B, a second guidewire 102 is advanced through the second catheter tip 82 such that the second guidewire 102 is wedged between the catheter tips 80, 82. In FIG. 14C, as the second guidewire 102 is advanced further, it urges the second catheter tip 82 away from the first catheter tip 80. Eventually the second catheter tip 82 is disassociated from the first catheter tip 80.

Figure 15:
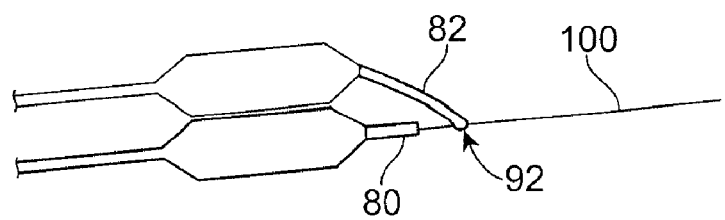
FIG. 15 is a side elevation view of a distal end region of a stent delivery system, the view showing a distal tip of a balloon attached to a guidewire lumen extending through another balloon.

In FIG. 15, an embodiment of a tip configuration is shown in which a first guidewire 100 is passed through a tip slit 92 such that the first guidewire 100 is nestled within the distal end of the second catheter tip 82. This configuration results in a reduced overall profile and eliminates the need for an additional component to associate the catheter tips and improves overall system stiffness and deliverability.

Figure 16A:
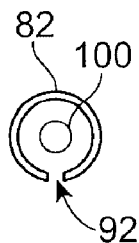
FIGS. 16A-16C are cross-sectional views of a distal end region of a stent delivery system, the views showing a method of attaching a distal tip of a balloon to a guidewire associated with another balloon and urging the distal tip to detach from the guidewire through the use of another guidewire.
Figure 16B:
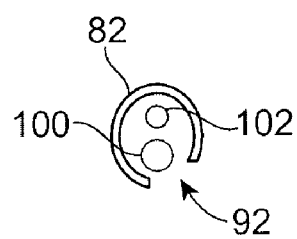
Figure 16C:
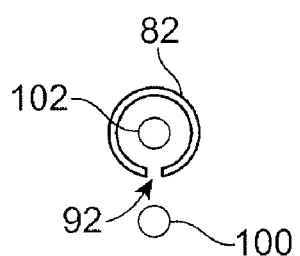

FIGS. 16A-16C show a method of disassociating a first guidewire 100 and a second catheter tip 82. In FIG. 16A, the second catheter tip 82 is disposed about the first guidewire 100, such as in the manner shown in FIG. 15. In FIG. 16B, a second guidewire 102 is advanced through the second catheter tip 82 so that the second guidewire wedges between the second catheter tip 82 and the first guidewire 100. In FIG. 16C, as the second guidewire 102 is advanced further, it urges the second catheter tip 82 away from the first guidewire 100. Eventually, the second catheter tip 82 is disassociated from the first guidewire 100.

Figure 17:
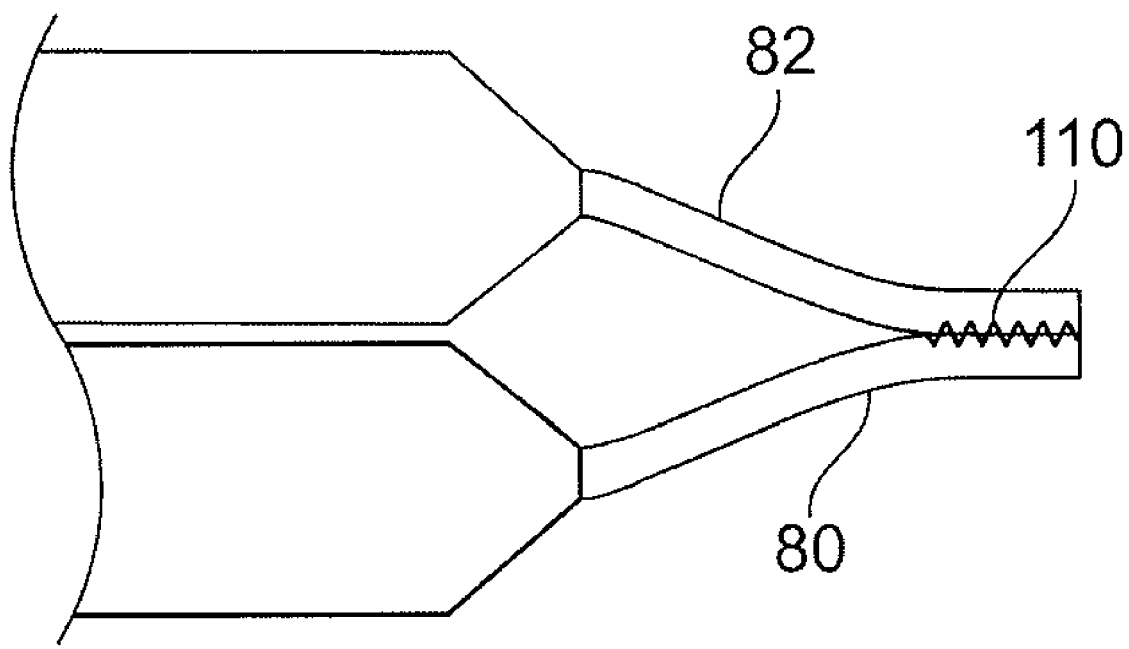
FIG. 17 is a side elevation view of a distal end region of a stent delivery system, the view showing an association feature that connectively associates balloon catheter tips until a sufficient force is applied to separate the balloon catheter tips.

In accordance with another embodiment of the present invention, the first and second catheter tips 80, 82 can be adjacently associated by a tip association feature 110, as shown in FIG. 17. The association feature 110 may be created by various processes. For example, the first and second catheter tips 80, 82 can be adjacently aligned and heated by a laser welder, which would result in a weld between the catheter tips. The weld can also be created by using thermal welding equipment. Further still, additional welding processes, such as white light welding, can be utilized in order to achieve a similar corrective effect. Further still, the connective association between the catheter tips 80, 82 can be created using an adhesive applied between the catheter tips while they are adjacently aligned. Other processes, including processes well known in the art, can be used to keep the catheter tips 80, 82 together while the they are introduced into an anatomical lumen and positioned at a desired anatomical location, such as near a bifurcation.

The tip association feature 110 of FIG. 17 is preferably destructible so that when a sufficient radial force is applied to the catheter tips 80, 82, the catheter tips will disassociate. The radial force can be applied for example by tracking and advancing the catheter tips 80, 82 over separate guidewires that take diverging paths at a bifurcated vessel.

Figure 18A:
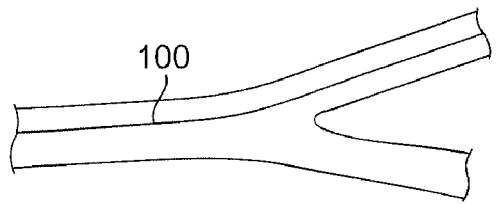
FIGS. 18A-18G show a method of delivering and deploying a stent in a bifurcated vessel using a stent delivery system having balloon catheter tips that are connected to each other when passing through a vessel and are disconnected from each other when they have reached the bifurcation.

FIGS. 18A-18G show a method for deploying a stent 32 within a bifurcated vessel using a stent delivery system 10 having connectively associated catheter tips 80, 82. In FIG. 18A, a first guidewire 100 is placed within a first branch of the bifurcated vessel.

Figure 18B:
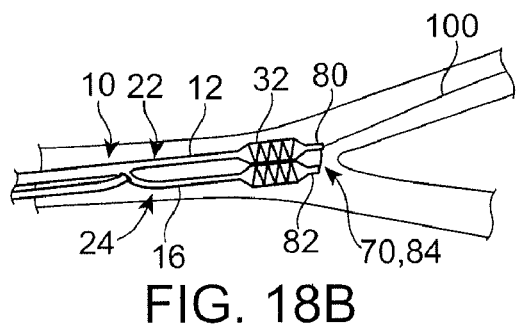

In FIG. 18B, the first guidewire 100 has been inserted within the first guidewire lumen 22. The stent delivery system 10 can be advanced over the first guidewire 100 to the ostium of the bifurcated vessel.

Figure 18C:
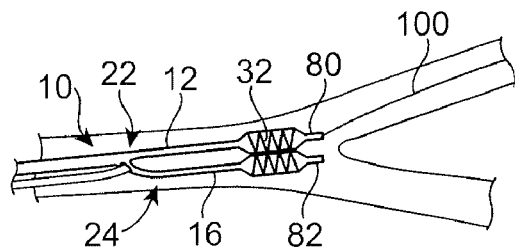

In FIG. 18C, a tensile load has been applied to the anchor element 70 or suture 84 such that the catheter tips 80, 82 are disassociated or disconnected from each other. Further still, the anchor element 70 or suture 84 can be entirely removed from the second catheter tip 82 and the second elongated shaft 16.

Figure 18D:
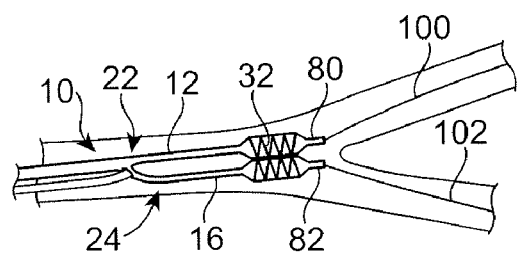

In FIG. 18D, a second guidewire 102 has been inserted within the second guidewire lumen 24 and advanced into a second branch of the bifurcated vessel.

Figure 18E:
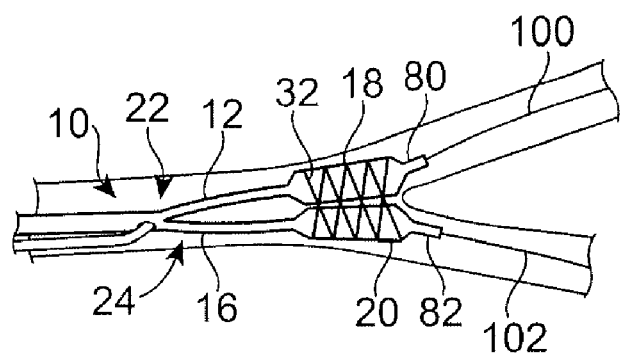

In FIG. 18E, the stent delivery system 10 has been advanced over the first and second guidewires 100, 102 to the ostium of the bifurcated vessel. The stent 32 is disposed about the first and second balloons 18, 20 and can be brought into contact with the carina of the bifurcation to ensure effective scaffolding of the ostium circumference.

Figure 18F:
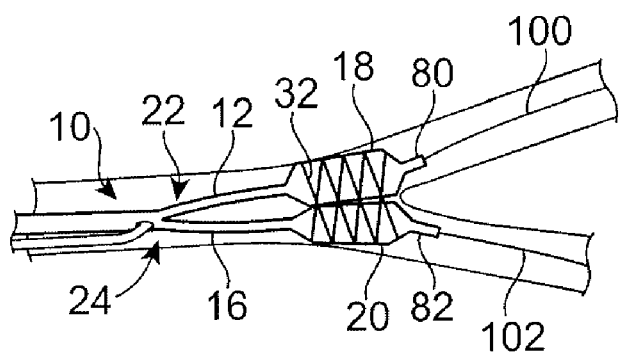

In FIG. 18F, fluid is introduced via a luer into an inflation lumen in fluid communication with the first and second balloons 18, 20. The luer is preferably located at a proximal end of the system 10. The introduced fluid eventually fills the first and second balloons 18, 20 such that the balloons expand, which, in turn, forces the stent 32 to expand and deploy at a selected location within the bifurcated vessel.

Figure 18G:
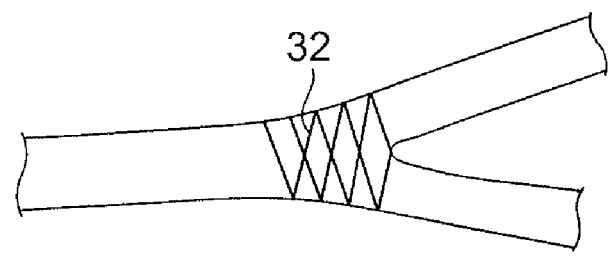

In FIG. 18G, fluid has been removed from the first and second balloons 18, 20 via the luer. Removal of fluid from the balloons 18, 20 causes them to contract or reduce in size. The stent delivery system 10 and guidewires 100, 102 have been removed from the anatomy, leaving the deployed stent 32 in place. Optionally and not necessarily, the guidewires 100, 102 may be left in the anatomy to facilitate subsequent treatment of the bifurcation with another device.

It will be understood that the invention described above is useful for treating disease within a bifurcated vessel. The embodiments in accordance with the present invention provide a delivery system with improved deliverability that provides optimized vessel coverage by the deployed stent.

Further, it will be understood that the invention described above can also be useful for treating a bifurcated vessel without a stent. For example, the system can be advanced to the bifurcated vessel and the balloons can be expanded to dilate a lesion at the bifurcated vessel. This could be useful in a pre-dilation procedure. This could also be useful in combination with drug eluting balloon technologies, in which no stent is required for effective vessel treatment.

It will be further understood that the present invention encompasses many embodiments. These embodiments may be useful alone or in combination.

The above descriptions are intended to be illustrative and not exhaustive. While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A medical device comprising:
    a first shaft including a proximal segment, a distal segment and a transition portion disposed between the proximal and distal segments;
    a second shaft attached to the first shaft at a location about the transition portion;
    a first balloon on the distal segment of the first shaft;
    a second balloon on the second shaft a first guidewire lumen associated with the first balloon;
    a second guidewire lumen associated with the second balloon, the second guidewire lumen terminating in a proximal aperture located on the second shaft; and
    a third guidewire lumen having a distal end disposed in the proximal aperture of the second shaft.

2. The medical device of claim 1, wherein the third guidewire lumen is removably coupled to the first shaft and is in communication with the second guidewire lumen.

3. The medical device of claim 2, wherein the third guidewire lumen is removably coupled to the first shaft by a coupling device including a first tubular wall defining a guidewire passageway, a second tubular wall sized to receive the first shaft, and an axially extending opening formed through at least a portion of the second tubular wall.

4. The medical device of claim 3, wherein an axially extending slit is formed through at least a portion of the first tubular wall.

5. The medical device of claim 2, wherein the third guidewire lumen includes a tubular wall retaining the first shaft, the tubular wall includes an axially extending opening adjacent the first shaft, and wherein a guidewire passageway is defined by an inner surface of the tubular wall and an outer surface of the first shaft.

6. The medical device of claim 5, wherein the tubular wall includes an inwardly protruding portion disposed between the guidewire passageway and the first shaft.

7. The medical device of claim 1, further comprising a distal tip attached to either one of the first balloon or the second balloon, the distal tip including a wall configured to retain a guidewire associated with the other one of the first balloon or the second balloon.

8. A medical device comprising:
    a first shaft including a proximal segment, a distal segment, and a transition portion disposed between the proximal and distal segments;
    a second shaft attached to the first shaft at a location about the transition portion;
    a first balloon on the distal segment of the first shaft;
    a second balloon on the second shaft;
    a catheter tip extending from either one of the first balloon or the second balloon; and
    a housing member attached to the other one of the first balloon or the second balloon, the housing member having a tubular wall and a slit formed through the tubular wall, the tubular wall configured to retain the catheter tip wherein the tubular wall of the housing member defines an end portion of a guidewire passageway, and the tubular wall is configured to release the catheter tip when a guidewire is advanced within the end portion of the guidewire passageway and is wedged between the catheter tip and the tubular wall.

9. A medical device comprising:
    a first shaft including a proximal segment, a distal segment, and a transition portion disposed between the proximal and distal segments;

a second shaft attached to the first shaft at a location about the transition portion;
a first balloon on the distal segment of the first shaft;
a second balloon on the second shaft; and
a distal tip attached to either one of the first balloon or the second balloon, the distal tip including a lumen and a wall, the wall configured to retain a first guidewire associated with the other one of the first balloon or the second balloon, wherein the wall of the distal tip defines an end portion of a guidewire passageway, and the wall is configured to release the first guidewire when a second guidewire is advanced out of the lumen of the distal tip and into the end portion of the guidewire passageway.

10. A medical device comprising:
a proximal shaft;
a first distal shaft attached to the proximal shaft;
a second distal shaft attached to the proximal shaft or the first distal shaft;
a first balloon adjacent a distal end of the first distal shaft, the first balloon having a first guidewire lumen;
a second balloon adjacent a distal end of the second distal shaft, the second balloon having a second guidewire lumen; and
a coupling device coupled to the first balloon, wherein the coupling device is configured to connect the distal end of the first distal shaft to a guidewire extending out of the second guidewire lumen, and the coupling device is configured to decouple the distal end of the first distal shaft from the guidewire when a second guidewire is advanced out of the first guidewire lumen and is wedged between the coupling device and the first-mentioned guidewire as it extends out of the second guidewire lumen.

11. The medical device of claim 10, wherein the coupling device is configured to decouple the distal end of the first distal shaft from the first-mentioned guidewire with application of a force to the coupling device by the second guidewire as it extends out of the first guidewire lumen.

12. The medical device of claim 10, further comprising a third guidewire lumen removably coupled to the proximal shaft, the third guidewire lumen in communication with the second guidewire lumen.

13. A method delivering a medical device, the method comprising:
tracking a catheter on a first guidewire, the catheter including a first shaft, a second shaft attached to the first shaft, a first guidewire lumen associated with a first balloon, and a second guidewire lumen associated with a second balloon, the first guidewire lumen extending through the first shaft, and the second guidewire lumen extending through the second shaft; and followed by disconnecting the first and second balloons from each other by decoupling a first device attached to the first balloon from a second device attached to the second balloon, wherein neither the first device nor the second device is the first guidewire on which tracking of the catheter was performed; wherein a removable guidewire lumen is coupled to the catheter by a coupling device including a tubular wall retaining the first shaft and defining a guidewire passageway, and wherein an axially extending opening is formed through at least a portion of the tubular wall.

14. A method of delivering a medical device, the method comprising:
tracking a catheter on a first guidewire, the catheter including a first shaft, a second shaft attached to the first shaft, a first guidewire lumen associated with a first balloon, and a second guidewire lumen associated with a second balloon, the first guidewire lumen extending through the first shaft, and the second guidewire lumen extending through the second shaft; and followed by disconnecting the first and second balloons from each other by decoupling a first device attached to the first balloon from a second device attached to the second balloon, wherein neither the first device nor the second device is the first guidewire on which tracking of the catheter was performed, wherein the first device is an anchor member and the second device is an anchor housing having a recess configured to retain the anchor member in manner such that a force applied to either one or both of the anchor member and the anchor housing causes the anchor member to be released from the anchor housing and wherein during the tracking, a distal tip of the anchor member is retained within the anchor housing.

15. A method of of delivering a medical device, the method comprising:
tracking a catheter on a first guidewire, the catheter including a first shaft, a second shaft attached to the first shaft, a first guidewire lumen associated with a first balloon, and a second guidewire lumen associated with a second balloon, the first guidewire lumen extending through the first shaft, and the second guidewire lumen extending through the second shaft; and followed by disconnecting the first and second balloons from each other by decoupling a first device attached to the first balloon from a second device attached to the second balloon, wherein neither the first device nor the second device is the first guidewire on which tracking of the catheter was performed, wherein the first device is a suture and the second device is an eyelet feature, and wherein the suture passes through the eyelet feature.

16. A method of of delivering a medical device, the method comprising:
tracking a catheter on a first guidewire, the catheter including a first shaft, a second shaft attached to the first shaft, a first guidewire lumen associated with a first balloon, and a second guidewire lumen associated with a second balloon, the first guidewire lumen extending through the first shaft, and the second guidewire lumen extending through the second shaft; and followed by disconnecting the first and second balloons from each other by decoupling a first device attached to the first balloon from a second device attached to the second balloon, wherein neither the first device nor the second device is the first guidewire on which tracking of the catheter was performed, wherein the first device is catheter tip and the second device is a housing member having a tubular wall and a slit formed through the tubular wall, the tubular wall is configured to retain the catheter tip, the tubular wall defines an end portion of a guidewire passageway, and the tubular wall is configured to release the catheter tip when a second guidewire is advanced within the end portion of the guidewire passageway.

17. A method of delivering a medical device, the method comprising:
tracking a catheter on a first guidewire, the catheter including a first shaft, a second shaft attached to the first shaft, a first guidewire lumen extending through the first shaft and associated with a first balloon, and a second guidewire lumen extending through the second shaft and associated with a second balloon, the first guidewire extending through the first guidewire lumen and connected to a distal tip of the second balloon, the distal tip including a wall retaining the first guidewire, the wall of the distal tip defining an end portion of a guidewire passageway; and followed by disconnecting the first guidewire from the distal tip of the second balloon by advancing a second guidewire through the second guidewire lumen and into the end portion of the guidewire passageway.

* * * * *